United States Patent [19]

Bromwich

[11] 4,056,972
[45] Nov. 8, 1977

[54] TESTING OF INACCESSABLE PARTS

[75] Inventor: Robert Alan Charles Bromwich, Marlow, England

[73] Assignee: Foster Wheeler Energy Corporation, Livingston, N.J.

[21] Appl. No.: 700,946

[22] Filed: June 29, 1976

[30] Foreign Application Priority Data

July 4, 1975 United Kingdom ............... 28364/75

[51] Int. Cl.² ............................................ G01N 29/04
[52] U.S. Cl. .................................. 73/620; 176/19 R; 73/629
[58] Field of Search ................... 73/67.8 S; 176/19 R; 324/37 R, 40 R

[56] References Cited

U.S. PATENT DOCUMENTS

| 3,056,285 | 10/1962 | Gibson | 73/67.8 S |
| 3,990,301 | 11/1976 | Smith | 73/67.8 S |

FOREIGN PATENT DOCUMENTS 2,101,169   8/1972   Germany ........................... 176/19 R Primary Examiner—James J. Gill
Attorney, Agent, or Firm—Marvin A. Naigur; John E. Wilson

[57] ABSTRACT

It is often necessary to test by means of probes such as an ultra sonic probe or an eddy current probe, an inaccessable part of a heat exchanger within a shell. The apparatus according to the invention can be inserted through small holes such as available hand-holes and then fixed in place within the shell. The apparatus has a clamp, a hingeable arm which can be hinged straight for insertion through the hand-hole and then bent ready for use, the arm being rotatable relative the clamp and carrying a probe arm for the probe so that the probe can be taken progressively over the surface of the part being tested.

4 Claims, 4 Drawing Figures

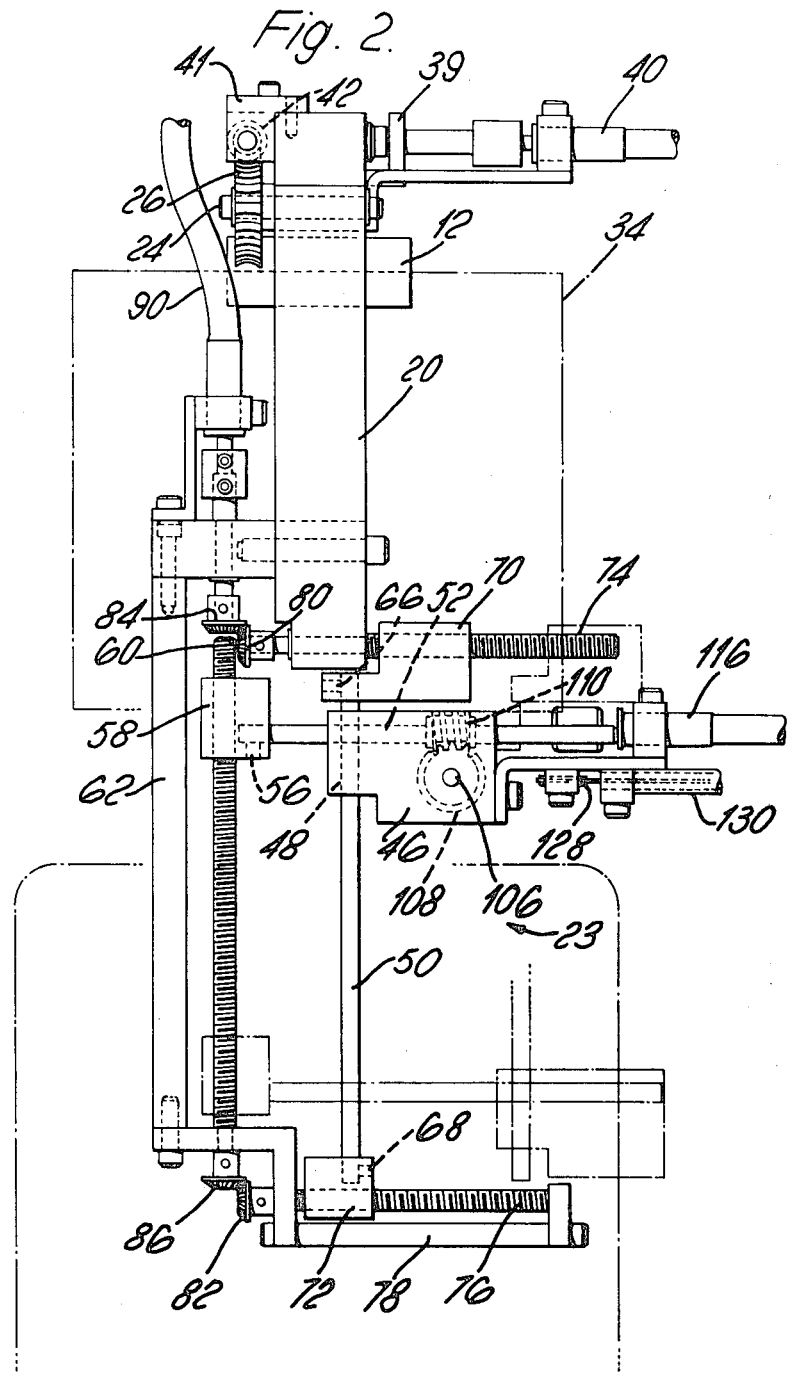

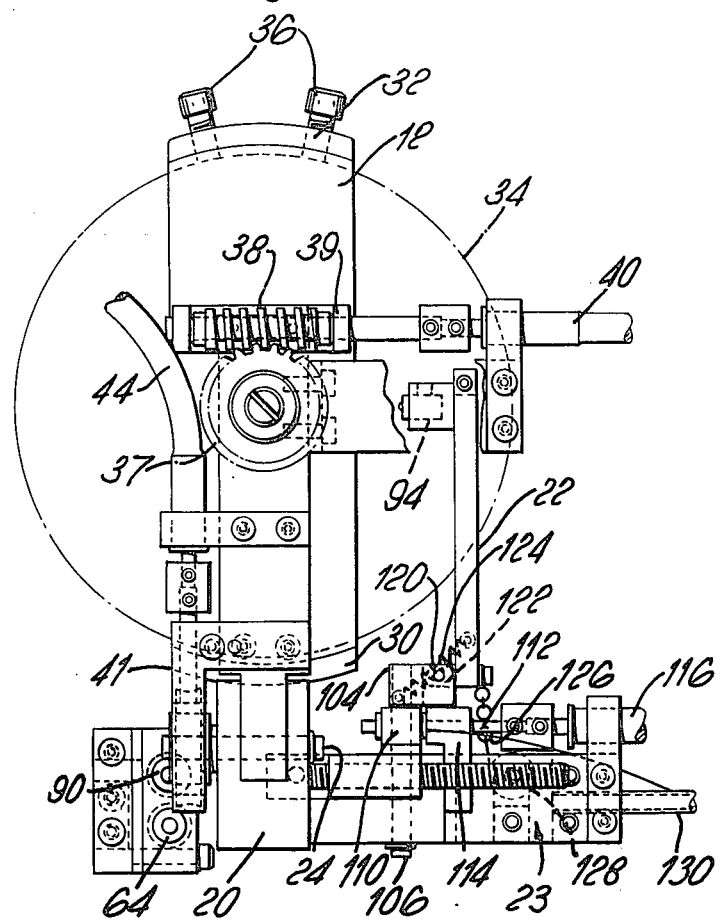
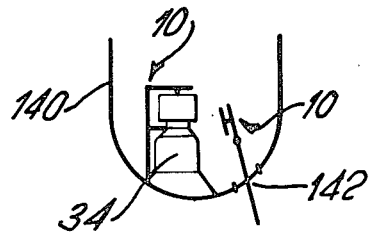

TESTING OF INACCESSABLE PARTS

This invention relates to the non-destructive testing of inaccessable parts.

BACKGROUND TO THE INVENTION

During fabrication and after a period of use it is desirable to test the interior parts in such items as heat exchangers and once such parts have been enclosed within their shell access to them is very difficult. This difficulty may be increased in the case where the heat exchangers have been used in nuclear power installations by the fact that, after a period of use, there may be some radioactive activity within the shell.

There are often small blanked-off hand-holes in the shell and these represent the only convenient access to the shell interior. Accordingly a testing apparatus must be capable of being passed through such a hand-hole.

One form of testing is to move a probe such as an ultra sonic or eddy current probe over the surface of a part to be tested to locate flaws.

BRIEF SUMMARY OF THE INVENTION

According to the invention there is provided apparatus for testing inaccessable parts comprising:
- a clamp which can be clamped in place on the part to be tested or another part fixed in relation to that part to be tested,
- a hingeable arm rotatably mounted on the clamp, means for hingeing that arm from a substantially straight configuration for insertion through restricted regions to a bent configuration for use,
- means for rotating the arm relative the clamp, and a probe arm carried on the hingeable part of the hingeable arm and movable once the arm is in the bent configuration relative the hingeable arm in directions parallel to the axis of rotation and tangential to circles whose axes are coincident with the axis of rotation, whereby during rotation of the hingeable arm a testing probe carried by the probe arm can be taken progressively over the surface of the part being tested.

When the hingeable arm is in its straight configuration the apparatus can be made small enough in the longitudinal direction of the arm to be inserted through confined access areas such as the hand-holes noted above. Once inside a shell, however, the apparatus can be clamped in position and the arm hinged to the bent configuration so that the probe can be taversed over the whole surface of the part requiring testing.

The two parts of the hingeable arm can be made to hinge by, for example, a worm meshing with a worm wheel, the worm being carried by one part and the worm wheel being fixed to the other.

It may be desirable for the probe arm to be hingedly fixed to the hingeable arm so that during insertion through a confined access area the probe arm can be hinged flat with the hingeable arm. It can then be moved to its operating position once the apparatus is in place and the movement between these two positions is conveniently controlled by a chain, bowden cable or the like.

To enable the probe to follow the contours of the part being examined, the probe must be able to move longitudinally of and at right angles to the hingeable part of the hingeable arm. This can be achieved by mounting the probe arm on a block which is the movable part of a 2-way plotter mechanism carried by the hingeable part of the arm.

Because all of the surfaces of the part to be tested are not likely to be parallel to the axis of rotation, it is desirable to orient the probe at right angles to the portion of the surface being tested at any instant. This can be achieved by rotatably mounting the probe arm and controlling the orientation of the probe arm by a meshing worm and worm wheel, rotation of the worm altering the orientation of the probe.

BRIEF DESCRIPTION OF THE DRAWINGS

Test apparatus according to the invention will now be described, by way of example, with reference to the accompanying drawings, in which:

FIG. 2 in an end elevation;

FIG. 3 is a plan; and

FIG. 4 is a diagram illustrating the use of the apparatus of the invention.

DESCRIPTION OF THE PREFERRED EMBODIMENT

Figure 1:
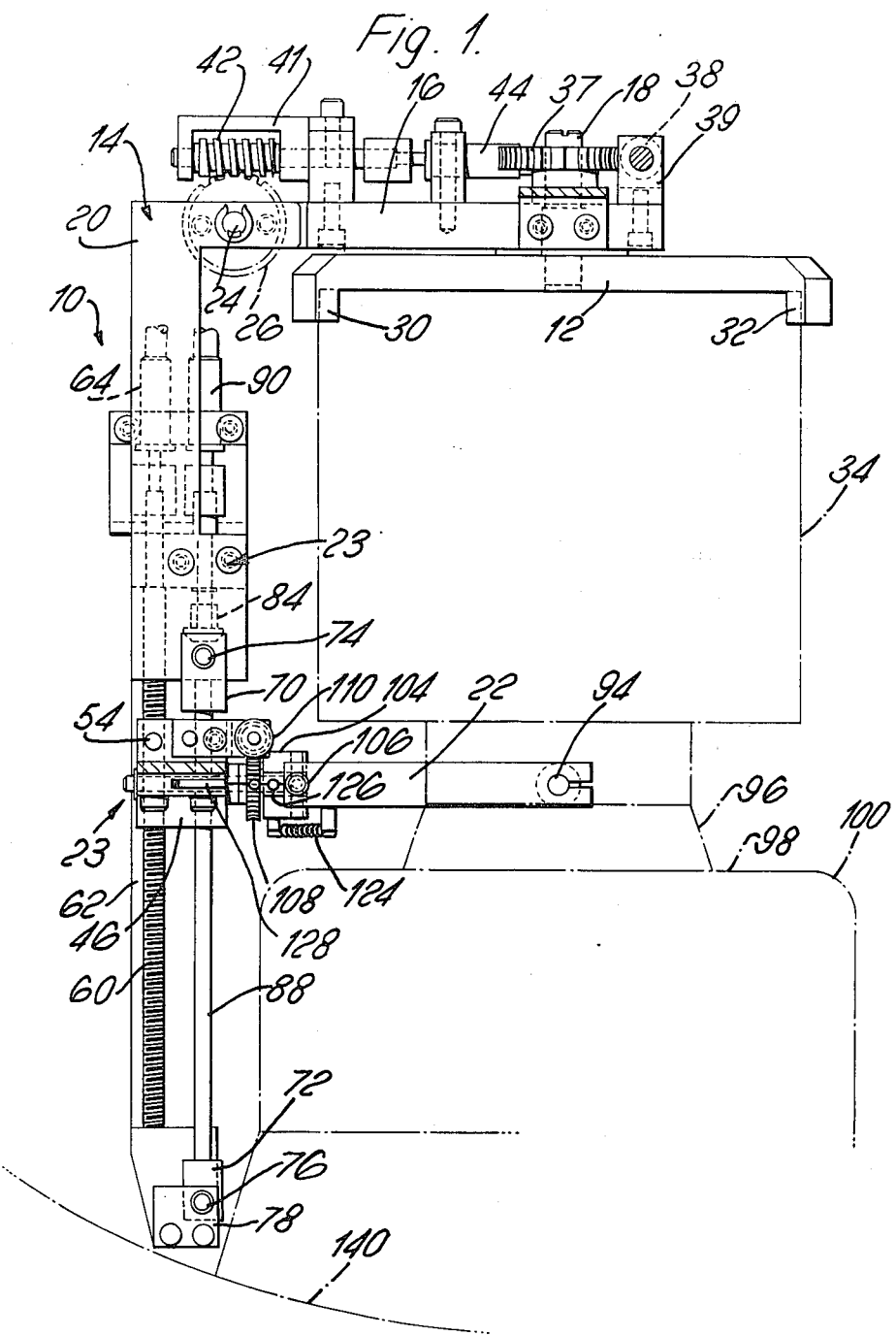
FIG. 1 is a side elevation of the apparatus in its working position.

The testing apparatus 10 shown in FIG. 1 to 3 has a clamp 12 about which is rotatable a hinged arm 14. The latter is in two parts, a part 16 which is rotatably mounted on a pin 18 upstanding from the clamp and a part 20 carrying a probe arm 22 by means of a 2-way plotter mechanism 23. The two parts are hinged to one another about a spindle 24 on which is mounted a worm wheel 26 fast with the part 20.

The clamp 12 has two lugs 30 and 32 which fit over the part 34 to be tested and through the lug 32 are screwed two bolts 36 which can be tightened to grip the clamp on the top of the part 34.

Fixed on the pin 18 is a worm wheel 37 and engaged with it is a worm 38 journalled in a bracket 39 fitted on the part 16 of the arm 14. The worm 38 is driven by means of a cable drive 40. Therefore drive of the latter causes the arm 14 to rotate about the pin 18 relative the clamp.

Rotatably journalled in a bracket 41 mounted on the part 16 and meshing with the worm wheel 26 is a worm 42. This is driven by a cable drive 44. Thus upon rotation of the worm 42, the part 20 of the arm can be hinged about the spindle 24 between an operating position as shown in FIGS. 1 to 3 where the two parts define a right angle between them and a straightened configuration for insertion through confined access areas.

The 2-way plotter mechanism 23 comprises a locating block 46 on which the probe arm 22 is mounted. Through this block is a bore 48 and a rod 50 extends therethrough to guide the block in directions parallel to the axis of rotation of the arm 14. A further bore 52 extends at right angles to the bore 48 and the block is slidably mounted on a rod 54 which extends through the bore. The rod 54 is fixed by means of a grub screw 56 in a bore in a nut 58 which is threaded on a threaded rod 60. The latter is journalled in a bracket 62 fixed to the part 20 and rotated by a cable drive 64. Thus by actuating the drive 64, the nut 58 travels up or down the rod 60 taking the rod 54 and block 46 with it, the block sliding up or down, respectively, the rod 50.

The ends of the rod 50 are held by grub screws 66 and 68 in nuts 70 and 72, respectively. These nuts are in turn threaded on two threaded rods 74 and 76, respectively.

The rod 74 is journalled in the part 20 while the rod 74 is journalled in a bracket 78 forming an extension at the lower end of the bracket 62. Identical bevel gears 80 and 82 are fixed to the rods 74 and 76 and these mesh with bevel gears 84 and 86 mounted on a common rod 88 journalled in the bracket 62. The rod 88 is driven by a cable drive 90. In this way rotation of the rod 88 causes identical rotations of the threaded rods 74 and 76 and the nuts 70 and 72 correspondingly move along those rods taking the rod 50 supporting the block 46 with them. In this way the block can be moved towards and away from the part 20, i.e. in a direction which is tangential to circles whose centres are coincident with the axis of rotation.

Carried by the prob arm 22 is a probe 94 such as an eddy current probe. This is taken around in contact with the surface of the part 34 during testing. As can be seen the part 34 has surfaces which are not parallel to the axis of rotation of the apparatus, such as the surfaces 96 and 98 and corner 100. To keep the probe at right angles to each surface, therefore, the arm, 22 is mounted on a bush 104 fixed on a pin 106 journalled in the block 46. Also mounted fast on the pin 106 is a worm wheel 108 and meshing with the latter is a worm 110. This is held on a spindle 112 journalled on a bracket 114 fixed to the block 46 and driven by a cable drive 116. In this way, rotation of the cable drive 116 will cause the worm wheel 108 to rotate relative the block 46 taking with it the bush 104, arm 22 and probe 94 so that the latter can be brought so that it is at a right angle to any surface on the part 34.

So that the arm 22 will take up less room when being inserted through confined areas, it can be folded flat against the mechanism 23 by pivoting a pivot pin 120 carried by the bush 104 and passing through a lug 122 fixed to the arm 22. The arm is pulled to its extended position against the action of a spring 124 by means of a small chain 126 which passes around a pulley 128 mounted on the block 46 and extending to a bowden cable 130.

FIG. 4 shows diagrammatically how the apparatus 10 can be used to test a part 34 positioned within a shell 140. The shell has a small hand-hole 142 and the apparatus 10 will just fit through the hole when the arm 14 is in a straight configuration. Once through the hole, the clamp is fitted on the top of the part 34 and the arm hinged to its working position shown in FIGS. 1 to 3. The arm 22 is also brought to its extended position by the cable 130. Then the plotter mechanism 23 can be operated by the cable 104 and 90 to bring the probe into contact with the part 34, the cable 116 being operated if necessary to bring the probe to right angles to the surface. Operation of the cable 40 will then rotate the arm 14 carrying the probe around in a circle. After one revolution, the mechanism 23 is actuated to index the probe to a new circle of contact with the part 34. Alternatively the probe can be taken helically over the part 34 by operating the plotter mechanism at the same time as rotating the arm.

As can be appreciated the apparatus 10 is simple and can assume a compact size for fitting through a confined access area such as the hand-hole 142. It can also be fitted in position, and removed, quickly and easily and so in the event of the shell 140 containing residual radio activity the operator need only be exposed to this for a minimum of time. After that the apparatus can be operated completely remotely. To follow the position of the probe a small television camera or an intrascope can be used to observe the area under test if so desired.

Instead of using the cable drives 40, 44, 104 and 116, the apparatus can be operated by small D.C. electric motors mounted on the apparatus. These can then be used to drive the various parts, power being supplied by flexible leads extending from an operating panel positioned remotely of the parts being tested.

A latitude of modification, change and substitution is intended in the foregoing disclosure and in some instances some features of the invention will be employed without a corresponding use of other features. Accordingly it is appropiate that the appended claims be construed broadly and in a manner consistent with the spirit and scope of the invention herein.

I claim:
1. Apparatus for testing inaccessable parts comprising:
   a. a clamp which can be clamped in place on the part to be tested or another part fixed in relation to that part to be tested,
   b. a hingeable arm rotatably mounted on said clamp,
   c. means for hingeing said arm from a substantially straight configuration for insertion through restricted regions to a bent configuration for use,
   d. means for rotating said arm relative said clamp, and
   e. a probe arm carried on the hingeable part of said hingeable arm and means for moving the probe arm in directions parallel to the axis of rotation and tangential to circles whose axes are coincident with the axis of rotation of said hinged arm relative said clamp once the hinged arm is in the bent configuration, whereby during rotation of the hingeable arm a testing probe carried by said probe arm can be taken progressively over the surface of said part being tested.

2. Apparatus according to claim 1 in which said probe arm is hingedly fixed to the hingeable part of said hingeable arm so that during insertion of the apparatus through a confined access area said probe arm can be hinged flat.

3. Apparatus according to claim 1 wherein said means for moving comprises a two-way plotter mechanism carried by said hingeable arm, said mechanism having a two-way movable part which carries said probe arm.

4. Apparatus according to claim 1 in which said probe arm is rotatably mounted relative said hingeable arm so that the orientation of a probe carried by said probe arm can be varied.

* * * * *